(12) United States Patent
Lynch et al.

(10) Patent No.: US 7,368,574 B2
(45) Date of Patent: *May 6, 2008

(54) SUBSTITUTED THIAZOLIDINEDIONE DERIVATIVE, PROCESS FOR ITS PREPARATION AND ITS PHARMACEUTICAL USE

(75) Inventors: Ian Robert Lynch, Harlow (GB); Michael John Sasse, Tunbridge Wells (GB); Bernadette Marie Choudary, Woodmansterne (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/536,313

(22) Filed: Sep. 28, 2006

(65) Prior Publication Data

US 2007/0037859 A1    Feb. 15, 2007

Related U.S. Application Data

(63) Continuation of application No. 11/205,426, filed on Aug. 17, 2005, now abandoned, which is a continuation of application No. 10/354,365, filed on Jan. 30, 2003, now abandoned, which is a continuation of application No. 10/071,339, filed on Feb. 8, 2002, now abandoned, which is a continuation of application No. 09/581,816, filed as application No. PCT/EP98/08153 on Dec. 14, 1998, now abandoned.

(30) Foreign Application Priority Data

Dec. 16, 1997  (GB) ................... 9726563.1

(51) Int. Cl.
*C07D 417/12*   (2006.01)
(52) U.S. Cl. .................................. 546/269.7
(58) Field of Classification Search ............. 546/269.7
See application file for complete search history.

(56) References Cited

U.S. PATENT DOCUMENTS

| | | | |
|---|---|---|---|
| 5,002,953 A | 3/1991 | Hindley | 514/275 |
| 5,741,803 A | 4/1998 | Pool et al. | 514/342 |
| 5,910,592 A | 6/1999 | Pool et al. | 546/269.7 |
| 6,288,095 B1 | 9/2001 | Hindley | 514/367 |
| 2002/0099081 A1 | 7/2002 | Blackler et al. | |
| 2002/0137940 A1 | 9/2002 | Blackler et al. | |

FOREIGN PATENT DOCUMENTS

| | | |
|---|---|---|
| EP | 0 306 228 B1 | 11/1999 |
| WO | WO 93/10254 | 3/1993 |
| WO | WO 94/05659 | 3/1994 |
| WO | WO 95/21603 | 8/1995 |
| WO | WO 02/26737 | 4/2002 |

OTHER PUBLICATIONS

Cantello, et al., "The Synthesis of BRL 49653—A Novel and Potent Antihyperglycaemic Agent". *Bioorganic & Medicinal Chemistry Letters*, 4(10): 1181-1184 (1994).
Haleblian, et al., "Pharmaceutical Applications of Polymorphism". *Journal of Pharmaceutical Sciences*, 58(8): 911-929 (1969).
Brittain, et al. Polymorphism in Pharmaceutical Solids, NY: Marcel Dekker, Inc., 1999, pp. 125-181, 183-226, 228-330, and 331-361.
Chemical & Engineering News, Feb. 2003, pp. 32-35.
US Pharmacopia, 1995, pp. 1843-1844.
Concise Encyclopedia Chemistry, pp. 872-873 (1993).
U.S. Appl. No. 10/321,055, filed Dec. 17, 2002, Blackler et al.
U.S. Appl. No. 10/030,323, filed Apr. 19, 2000, Blackler et al.
U.S. Appl. No. 10/048,123, filed Apr. 19, 2000, Blackler et al.
U.S. Appl. No. 10/030,877, filed Apr. 19, 2000, Blackler et al.
Ulicky et al. Comprehensive Dictionary of Physical Chemistry, NY: Prentice Hall, 1992, p. 21.
Vippagunta et al. "Crystalline Solids", Advanced Drug Delivery Reviews, 48 (2001), pp. 3-26.
Brittain et al., "Polymorphism in Pharmaceutical Solids, NY" Marcel Dekker, Inc., 1999, pp. 1-2.

*Primary Examiner*—Patricia L. Morris
(74) *Attorney, Agent, or Firm*—Kathryn L. Sieburth; Mary E. McCarthy; Charles M. Kinzig

(57) ABSTRACT

A hydrate of 5-[4-[2-(N-methyl-N-(2-pyridyl)amino) ethoxy]benzyl]thiazolidine-2,4-dione, maleic acid salt., characterized in that it:
(i) comprises water in the range of from 0.3 to 0.6 molar equivalents; and
(ii) provides an infra red spectrum containing peaks at 1757, 1331, 1290, 1211 and 767 cm$^{-1}$; and/or
(iii) provides a Raman spectrum containing peaks at 1758, 1610, 1394, 1316 and 1289 cm$^{-1}$; and/or
(iv) provides a solid state nuclear magnetic resonance spectrum containing chemical shifts substantially as set out in Table I herein; and/or
(v) provides an X-ray powder diffraction (XRPD) pattern substantially as set out in FIG. IV herein; a process for the preparation of such a compound, a pharmaceutical composition containing such a compound and the use of such a compound or composition in medicine.

5 Claims, 4 Drawing Sheets

Fig. 3  $^1$H Decoupled $^{13}$C CP-MAS Spectra of Hydrate

SUBSTITUTED THIAZOLIDINEDIONE DERIVATIVE, PROCESS FOR ITS PREPARATION AND ITS PHARMACEUTICAL USE

This application is a continuation of application Ser. No. 11/205,426, filed Aug. 17, 2005, abandoned, which is a continuation of application Ser. No. 10/354,365, filed Jan. 30, 2003, abandoned, which is a continuation of application Ser. No. 10/071,339, filed Feb. 8, 2002, abandoned, which is a continuation of application Ser. No. 09/581,816, filed Jun. 16, 2000, abandoned, which is a 371 of International Application No. PCT/EP98/08153, filed Dec. 14, 1998.

This invention relates to a novel pharmaceutical, to a process for the preparation of the pharmaceutical and to the use of the pharmaceutical in medicine.

International Patent Application, Publication Number WO94/05659 discloses certain thiazolidinedione derivatives having hypoglycaemic and hypolipidaemic activity including 5-[4-[2-(N-methyl-N-(2-pyridyl)amino)ethoxy]benzyl]thiazolidine-2,4-dione, maleic acid salt (hereinafter also referred to as "Compound (I)").

Figure 1:
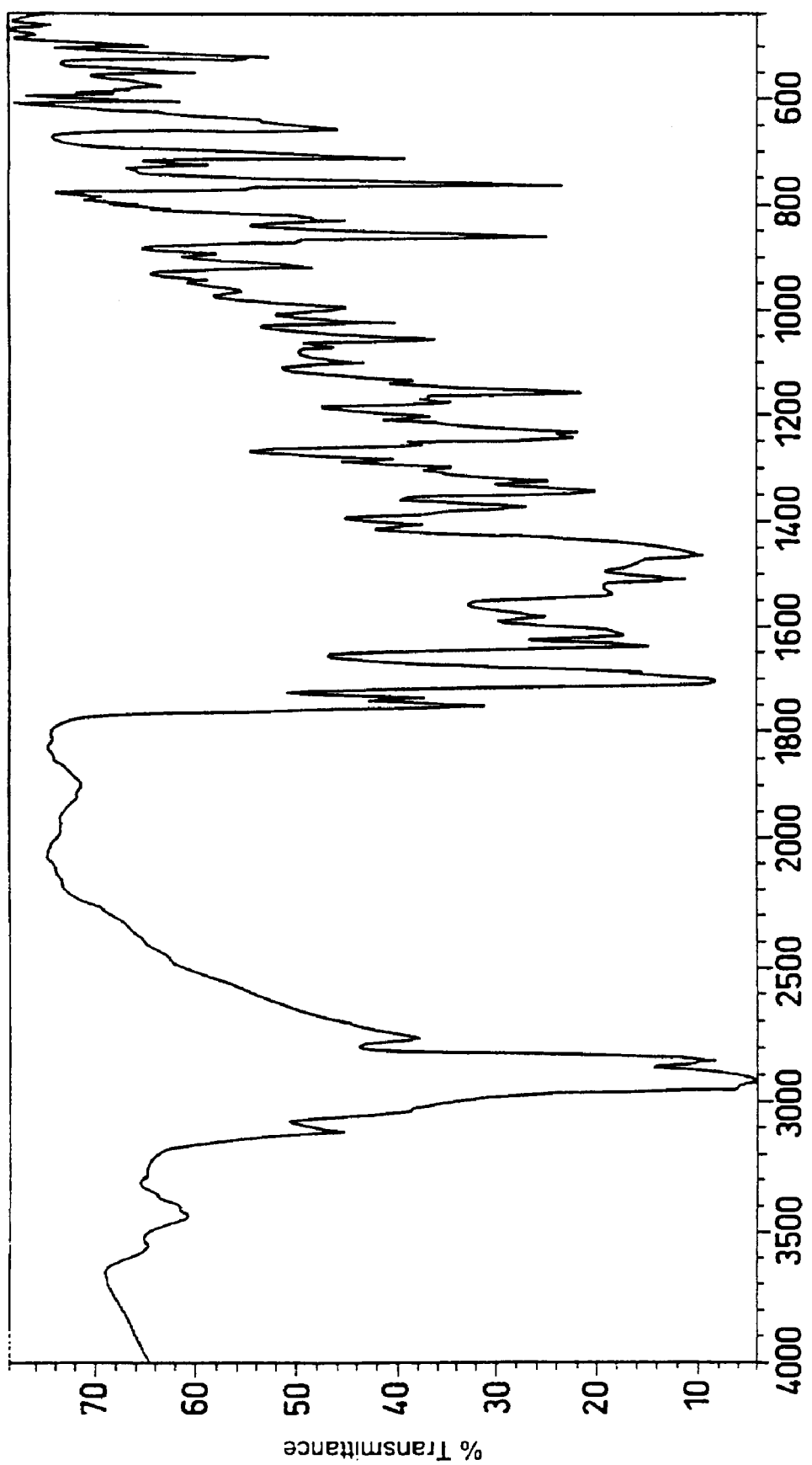
FIG. 1 is the infra red spectrum of a mineral oil dispersion of the crystalline Hydrate of this invention.
Figure 2:
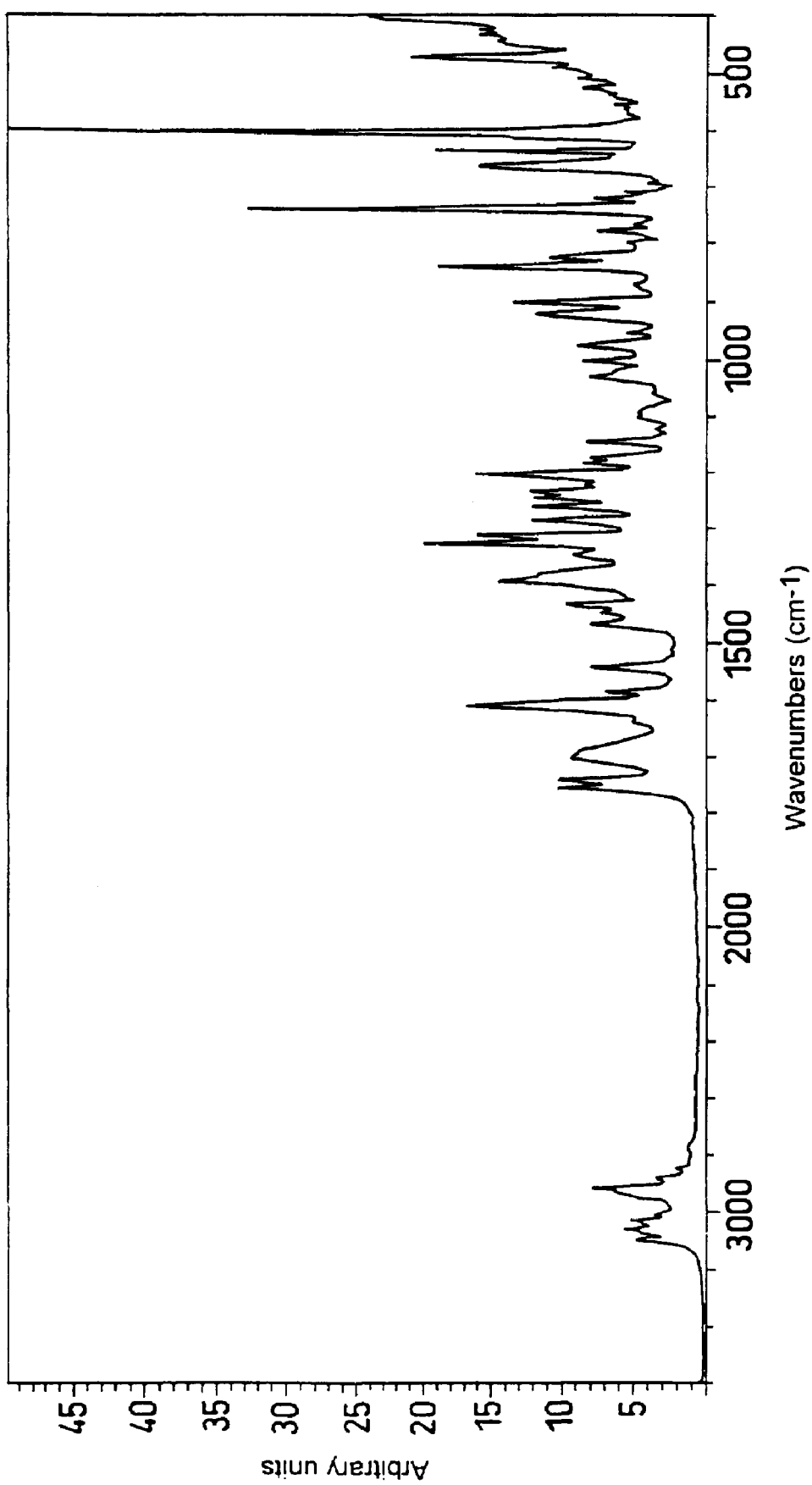
FIG. 2 is the Raman spectrum of the crystalline Hydrate of this invention.
Figure 3:
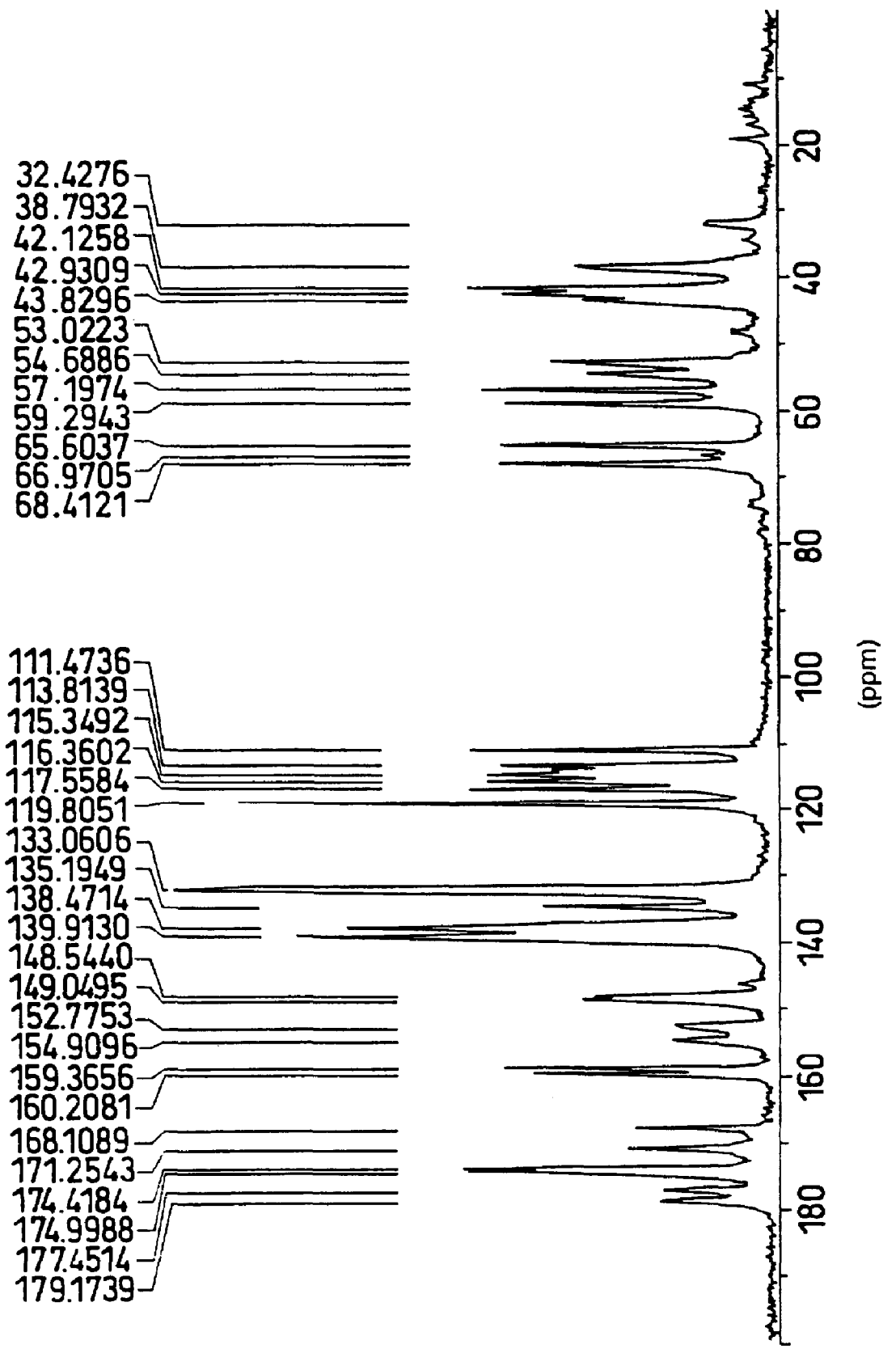
FIG. 3 is the solid state $^{13}C$ nuclear magnetic resonance spectrum of the crystalline Hydrate of this invention.
Figure 4:
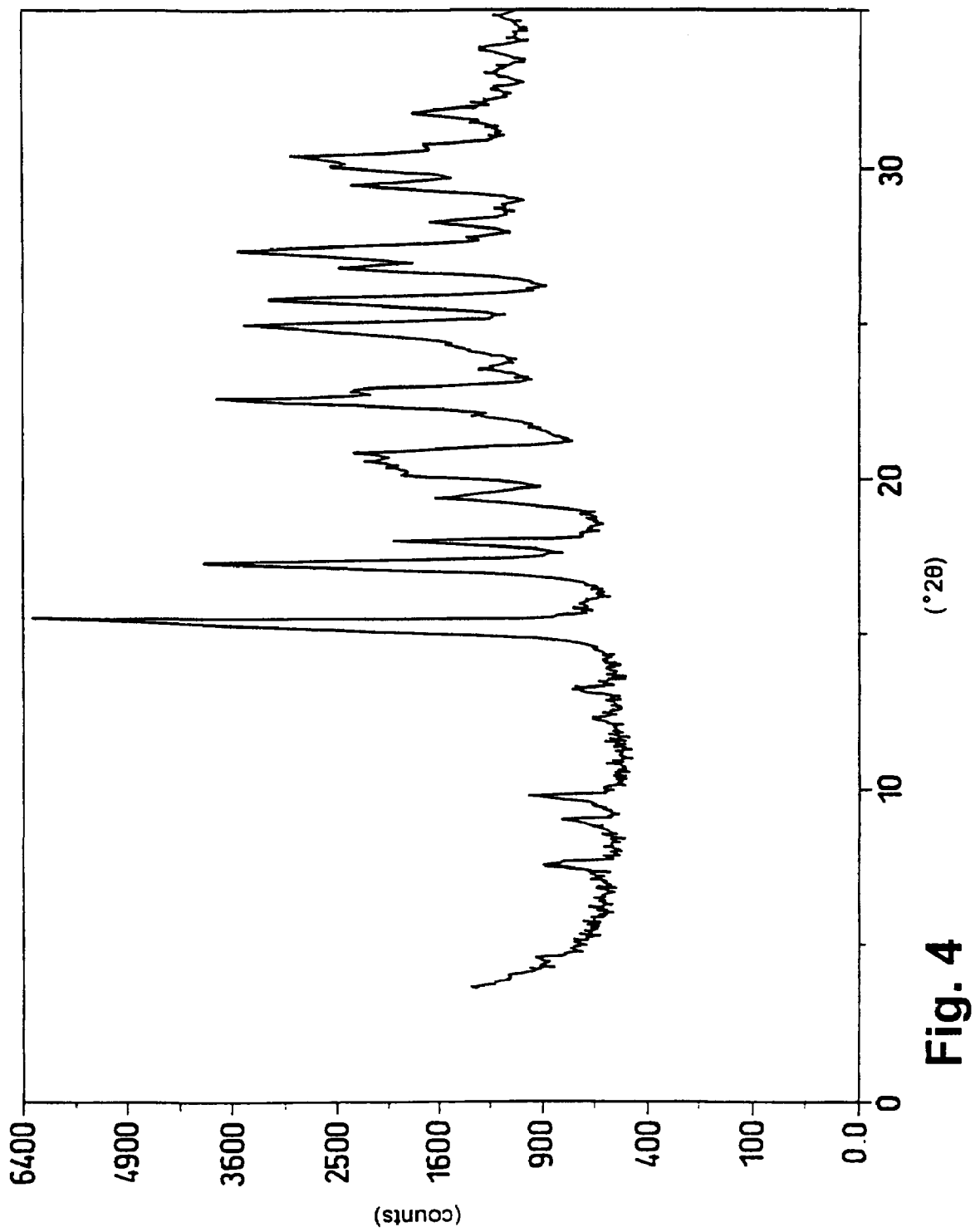
FIG. 4 is the X-ray powder diffraction (XRPD) pattern of the crystalline Hydrate of this invention.

Compound (I) is disclosed solely as an anhydrous form. It has now been discovered that Compound (I) exists in a novel hydrated form which is particularly suitable for bulk preparation and handling. This can be prepared by an efficient, economic and reproducible process particularly suited to large scale preparation.

The novel hydrate also has useful pharmaceutical properties and in particular it is indicated to be useful for the treatment and/or prophylaxis of diabetes mellitus, conditions associated with diabetes mellitus and certain complications thereof.

Accordingly, the present invention provides a hydrate of 5-[4-[2-(N-methyl-N-(2-pyridyl)amino)ethoxy]benzyl]thiazolidine-2,4-dione, maleic acid salt (the "Hydrate") characterised in that the Hydrate:
(i) comprises water in the range of from 0.3 to 0.6 molar equivalents; and
(ii) provides an infra red spectrum containing peaks at 1757, 1331, 1290, 1211 and 767 $cm^{-1}$; and/or
(iii) provides a Raman spectrum containing peaks at 1758, 1610, 1394, 1316 and 1289 $cm^{-1}$; and/or
(iv) provides a solid state nuclear magnetic resonance spectrum containing chemical shifts substantially as set out in Table I; and/or
(v) provides an X-ray powder diffraction (XRPD) pattern substantially as set out in FIG. IV.

Suitably, the water content of the Hydrate is in the range of from 0.3 to 0.5 molar equivalents, for example 0.4 molar equivalents.

In one favoured aspect, the Hydrate provides an infra red spectrum substantially in accordance with FIG. I.

In one favoured aspect, the Hydrate provides a Raman spectrum substantially in accordance with FIG. II.

In one favoured aspect, the Hydrate provides a solid state nuclear magnetic resonance spectrum substantially in accordance with FIG. III.

The Hydrate can exist in certain dehydrated forms which reversibly convert to the Hydrate when contacted with water, either in liquid or vapour form. The present invention encompasses all such reversibly rehydratable forms of the Hydrate.

The present invention encompasses the Hydrate isolated in pure form or when admixed with other materials, for example the known anhydrous form of Compound I, the above mentioned reversibly rehydratable forms or any other material.

Thus in one aspect there is provided the Hydrate in isolated form.

In a further aspect there is provided the Hydrate in pure form.

In yet a further aspect there is provided the Hydrate in crystalline form.

The invention also provides a process for preparing the Hydrate, characterised in that 5-[4-[2-(N-methyl-N-(2-pyridyl)amino)ethoxy]benzyl]thiazolidine-2,4-dione, maleic acid salt is crystallised from aqueous ethanol, conveniently aqueous denatured ethanol.

Suitably, the aqueous ethanol contains from 2% to 15% of water by volume, such as 5% to 15% of water by volume, favourably 7% to 12% of water by volume, preferably 10 to 12%, for example 10%.

Other aqueous solvents may also be used to prepare the Hydrate, for example isopropanol, acetonitrile, tetrahydrofuran, methyl ethyl ketone, ethyl acetate or acetic acid, or mixtures thereof. The precise amount of water used in each of the alternative solvents will depend upon the particular solvent chosen but typically it is in the range of from 2 to 15% of water by volume of water, for example 3%. For certain solvents, such as in ethyl acetate, water levels as low as 1% by volume can provide the Hydrate (thus providing a suitable range of 1 to 15% of water by volume in the appropriate solvent). Alternatively, the Hydrate can be obtained by crystallization from water containing a small amount (for example 2 to 5% by volume) of an organic acid such as acetic acid.

Crystallisation and any recrystallization is generally carried out at low to ambient temperature, such as in the range of between 0 to 30° C. for example 25° C.; alternatively crystallisation may be initiated at an elevated temperature, such as in the range of between 30° C. and 60° C. for example 50° C., and then completed by allowing the temperature of the solvent to cool to ambient or low temperature, such as in the range of between 0 to 30° C. for example 20° C.

The crystallisation can be initiated by seeding with crystals of the Hydrate but this is not essential.

Compound I is prepared according to known procedures, such as those disclosed in WO94/05659. The disclosures of WO94/05659 are incorporated herein by reference.

When used herein the term 'prophylaxis of conditions associated with diabetes mellitus' includes the treatment of conditions such as insulin resistance, impaired glucose tolerance, hyperinsulinaemia and gestational diabetes.

Diabetes mellitus preferably means Type II diabetes mellitus.

Conditions associated with diabetes include hyperglycaemia and insulin resistance, especially acquired insulin resistance and obesity. Further conditions associated with diabetes include hypertension, cardiovascular disease, especially atherosclerosis, certain eating disorders, in particular the regulation of appetite and food intake in subjects suffering from disorders associated with under-eating, such as anorexia nervosa, and disorders associated with over-eating, such as obesity and anorexia bulimia. Additional conditions associated with diabetes include polycystic ovarian syndrome and steroid induced insulin resistance.

The complications of conditions associated with diabetes mellitus encompassed herein includes renal disease, especially renal disease associated with the development of Type II diabetes including diabetic nephropathy, glomerulonephritis, glomerular sclerosis, nephrotic syndrome, hypertensive nephrosclerosis and end stage renal disease.

As used herein 'aqueous' with reference to a given solvent or solvent mixture refers to a solvent which contains sufficient water to provide Hydrate i.e having from 0.3 to 0.6 molar equivalents of water.

As mentioned above the compound of the invention has useful therapeutic properties: The present invention accordingly the Hydrate for use as an active therapeutic substance.

More particularly, the present invention provides the Hydrate for use in the treatment and/or prophylaxis of diabetes mellitus, conditions associated with diabetes mellitus and certain complications thereof.

The Hydrate may be administered per se or, preferably, as a pharmaceutical composition also comprising a pharmaceutically acceptable carrier. The formulation of the Hydrate and dosages thereof are generally as disclosed for Compound (I) in International Patent Application, Publication Number WO94/05659.

Accordingly, the present invention also provides a pharmaceutical composition comprising the Hydrate and a pharmaceutically acceptable carrier therefor.

The Hydrate is normally administered in unit dosage form.

The active compound may be administered by any suitable route but usually by the oral or parenteral routes. For such use, the compound will normally be employed in the form of a pharmaceutical composition in association with a pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

In addition such compositions may contain further active agents such as anti-hypertensive agents and diuretics.

As is common practice, the compositions will usually be accompanied by written or printed directions for use in the medical treatment concerned.

As used herein the term 'pharmaceutically acceptable' embraces compounds, compositions and ingredients for both human and veterinary use: for example the term 'pharmaceutically acceptable salt' embraces a veterinarily acceptable salt.

The present invention further provides a method for the treatment and/or prophylaxis of diabetes mellitus, conditions associated with diabetes mellitus and certain complications thereof, in a human or non-human mammal which comprises administering an effective, non-toxic, amount of Hydrate to a human or non-human mammal in need thereof.

Conveniently, the active ingredient may be administered as a pharmaceutical composition hereinbefore defined, and this forms a particular aspect of the present invention.

In the treatment and/or prophylaxis of diabetes mellitus, conditions associated with diabetes mellitus and certain complications thereof. Hydrate may be taken in doses, such as those described above.

Similar dosage regimens are suitable for the treatment and/or prophylaxis of non-human mammals.

In a further aspect the present invention provides the use of Hydrate for the manufacture of a medicament for the treatment and/or prophylaxis of diabetes mellitus, conditions associated with diabetes mellitus and certain complications thereof.

No adverse toxicological effects are indicated in the above mentioned treatments for the compounds of the invention.

The following examples illustrate the invention but do not limit it in any way.

EXAMPLE 1

Preparation of Hydrate of 5-[4-[2-(N-methyl-N-(2-pyridyl)amino)ethoxy]benzyl]thiazolidine-2,4-dione, maleic acid salt 5-[4-[2-(N-methyl-N-(2-pyridyl)amino)ethoxy]benzyl] thiazolidine-2,4-dione free base (6.0 g) and maleic acid (2.1 g) were heated to 60° C. in denatured ethanol (60 ml) containing additional water (6.1 ml, i.e. a total water content of approximately 10% (v/v)), and stirred at this temperature for 30 minutes during which a solution was obtained. The solution was filtered, re-heated to 55° C., and then cooled to 20-25° C. and stirred for eighteen hours. The product was filtered and dried at 50° C. in vacuo to give the title compound (4.62 g, 58%).

CHARACTERISING DATA: The following characterising data were generated for the Hydrate:

A Water content

This was determined as 1.55% w/w (0.41 molar equivalents) using a Karl Fischer apparatus.

B Infrared

The infrared absorption spectrum of a mineral oil dispersion of the Hydrate was obtained using a Nicolet 710 FT-IR spectrometer at 2 cm$^{-1}$ resolution. Data were digitised at 1 cm$^{-1}$ intervals. The spectrum obtained is shown in FIG. I. Peak positions are as follows: 3574, 3458, 3377, 3129, 2776, 1757, 1743, 1708, 1691, 1640, 1620, 1585, 1542, 1512, 1414, 1350, 1331, 1306, 1290, 1249, 1238, 1211, 1183, 1163, 1143, 1107, 1078, 1063, 1031, 1002, 974, 954, 927, 902, 865, 836, 830, 817, 809, 767, 735, 717, 663, 616, 585, 558, 520 and 508 cm$^{-1}$.

C Raman

A Raman spectrum of the Hydrate was recorded through glass vials using a Perkin Elmer 2000R spectrometer at 4 cm$^{-1}$ resolution and is shown in FIG. II (1800-200 cm$^{-1}$). Excitation was achieved using a Nd:YAG laser (1064 nm) with a power output of 500 mW. Data were digitised at 1 cm$^{-1}$ intervals. Peak positions are as follows: 1758, 1743, 1703, 1610, 1586, 1544, 1468, 1435, 1394, 1330, 1316, 1289, 1265, 1238, 1206, 1185, 1148, 1095, 1032, 1003, 976, 923, 903, 843, 825, 780, 741, 722, 664, 637, 606, 526, 471, 403, 331 and 293 cm$^{-1}$.

D NMR

The 90.55 MHz $^{13}$C CP-MAS NMR spectrum for the Hydrate is shown below in FIG. III. Chemical shifts are tabulated in Table I. Data were recorded at ambient temperature and 10 kHz spinning frequency, without prior grinding of the sample, on a Bruker AMX360WB spectrometer, with 1.6 ms cross polarization, and a repetition rate of 20 s. Chemical shifts were referenced to the high-field resonance of solid adamantane (38.4 ppm relative to tetramethylsilane), and are judged accurate to within +/−0.5 ppm. Peaks were not assigned.

TABLE I $^{13}$C Chemical Shifts of the Hydrate

| Chemical Shift (ppm) |
| --- |
| 32.4 |
| 38.8 |
| 42.1 |
| 42.9 |
| 43.8 |
| 53.0 |
| 54.7 |
| 57.2 |
| 59.3 |
| 65.6 |
| 67.0 |
| 68.4 |
| 111.5 |
| 113.8 |
| 115.3 |
| 116.4 |
| 117.6 |
| 119.8 |
| 133.1 |
| 135.2 |
| 138.5 |
| 139.9 |
| 148.5 |
| 149.0 |
| 152.8 |
| 154.9 |
| 159.4 |
| 160.2 |
| 168.1 |
| 171.3 |
| 174.4 |
| 175.0 |
| 177.5 |
| 179.2 |

E X-Ray Powder Diffraction (XRPD)

The XRPD pattern of the Hydrate is shown below in FIG. IV and a summary of the XRPD angles and calculated lattice spacing characteristic of the Hydrate is given in Table II.

A PW1710 X-ray powder diffractometer (Cu X-ray source) was used to generate the spectrum using the following acquisition conditions:

| | |
| --- | --- |
| Tube anode: | Cu |
| Generator tension: | 40 kV |
| Generator current: | 30 mA |
| Start angle: | 3.5 ° 2θ |
| End angle: | 35.0 ° 2θ |
| Step size: | 0.020 |
| Time per step: | 4.550 s |

TABLE II

X-Ray Powder Diffraction Angles and Calculated Lattice Spacing Characteristic of the Hydrate.

| Diffraction Angle (° 2θ) | Lattice Spacing (Angstroms) |
| --- | --- |
| 7.5 | 11.74 |
| 9.8 | 9.04 |
| 15.2 | 5.81 |
| 17.2 | 5.15 |
| 17.9 | 4.95 |
| 19.3 | 4.60 |
| 20.4 | 4.35 |
| 20.7 | 4.29 |

TABLE II-continued

X-Ray Powder Diffraction Angles and Calculated Lattice Spacing Characteristic of the Hydrate.

| Diffraction Angle (° 2θ) | Lattice Spacing (Angstroms) |
|---|---|
| 22.3 | 3.98 |
| 24.8 | 3.59 |
| 25.6 | 3.47 |
| 26.6 | 3.35 |
| 27.1 | 3.29 |
| 28.1 | 3.17 |
| 29.3 | 3.05 |
| 30.2 | 2.96 |
| 31.6 | 2.83 |

EXAMPLE 2

The maleate salt of 5-[4-[2-(N-methyl-N-(2-pyridyl) amino)ethoxy]benzyl] thiazolidine-2,4,-dione anhydrate (3.0 g) was stirred and heated at 55-60° C. in acetonitrile (30 ml) containing water (1 ml) until complete dissolution was achieved. The resultant solution was stirred and cooled to 20-25° C. and the product was filtered, washed with acetonitrile (5 ml) and dried at 50° C. in vacuo to give the title compound (1.8 g, 60%). The water content of the product was 1.77%.

EXAMPLE 3

The procedure of Example 2 was repeated using tetrahydrofuran (15 ml) containing water (0.5 ml) as solvent. Yield 1.8 g (60%), water content 1.60%.

EXAMPLE 4

The procedure of Example 2 was repeated using methyl ethyl ketone (30 ml) containing water (1 ml) as solvent. Yield 2.05 g (68%), water content 1.58%.

EXAMPLE 5

The procedure of Example 2 was followed using 2.0 g maleate salt, heating to 65° C. in ethyl acetate (150 ml) containing water (1.5 ml) as solvent. Yield 1.34 g (67%), water content 1.61%.

EXAMPLE 6

The procedure of Example 2 was followed, heating to 65-70° C. in isopropanol (33 ml) containing water (1 ml) as solvent. Yield 2.4 g (80%), water content 1.58%.

EXAMPLE 7

The procedure of Example 2 was repeated using a mixture of water (20 ml) and acetic acid (1.0 g) as solvent. Yield 0.76 g (38%), water content 1.78%.

The invention claimed is:

1. A crystalline hydrate of 5-[4-[2-(N-methyl-N-(2-pyridyl) amino)ethoxy]benzyl]thiazolidine-2,4-dione, maleic acid salt, wherein said hydrate comprises water in the range of from 0.3 to 0.6 molar equivalents and provides at least one of:
   (i) an infra red spectrum containing peaks at 1757, 1331, 1290, 1211 and 767 $cm^{-1}$;
   (ii) a Raman spectrum containing peaks at 1758, 1610, 1394, 1316 and 1289 $cm^{-1}$;
   (iii) a solid state nuclear magnetic resonance spectrum containing chemical shifts substantially as set out in Table I; and
   (iv) an X-ray powder diffraction pattern substantially as set out in FIG. IV.

2. A hydrate according to claim 1, which comprises water in the range of from 0.3 to 0.5 molar equivalents.

3. A crystalline hydrate of 5-[4-[2-(N-methyl-N-(2-pyridyl) amino)ethoxy]benzyl]thiazolidine-2,4-dione, maleic acid salt, wherein said hydrate provides a Raman spectrum substantially in accordance with FIG. II.

4. A crystalline hydrate of 5-[4-[2-(N-methyl-N-(2-pyridyl) amino)ethoxy]benzyl]thiazolidine-2,4-dione, maleic acid salt, wherein said hydrate provides a solid state $^{13}C$ nuclear magnetic resonance spectrum substantially in accordance with FIG. III.

5. A crystalline hydrate of 5-[4-[2-(N-methyl-N-(2-pyridyl)amino) ethoxy]benzyl]thiazolidine-2,4-dion, maleic acid salt, wherein said hydrate provides an X-ray powder diffraction pattern substantially as set out in FIG. IV.

* * * * *